United States Patent
Castillo

(10) Patent No.: US 9,616,184 B2
(45) Date of Patent: Apr. 11, 2017

(54) SYRINGE FACILITATING RETRACTION OF MULTIPLE NEEDLES

(71) Applicant: Hilario Castillo, New Rochelle, NY (US)

(72) Inventor: Hilario Castillo, New Rochelle, NY (US)

( * ) Notice: Subject to any disclaimer, the term of this patent is extended or adjusted under 35 U.S.C. 154(b) by 0 days.

(21) Appl. No.: 14/179,541

(22) Filed: Feb. 12, 2014

(65) Prior Publication Data

US 2014/0228804 A1 Aug. 14, 2014

Related U.S. Application Data

(60) Provisional application No. 61/763,984, filed on Feb. 13, 2013.

(51) Int. Cl.
*A61M 5/32* (2006.01)

(52) U.S. Cl.
CPC ........ *A61M 5/3298* (2013.01); *A61M 5/3221* (2013.01); *A61M 5/3232* (2013.01)

(58) Field of Classification Search
CPC .............. A61M 5/3232; A61M 5/3221; A61M 2005/004; A61M 2005/005; A61M 5/3295; A61M 5/3297; A61M 5/3298; A61M 5/008; A61M 2005/3206
USPC ....... 604/198, 117, 171, 173, 272, 506, 191, 604/192, 232
See application file for complete search history.

(56) References Cited

U.S. PATENT DOCUMENTS

| | | | |
|---|---|---|---|
| 5,030,208 A | 7/1991 | Novacek | |
| 5,300,038 A | 4/1994 | Haber et al. | |
| 6,010,486 A * | 1/2000 | Carter | A61M 5/3234 604/110 |
| 6,428,517 B1 | 8/2002 | Hochman et al. | |
| 2010/0168616 A1* | 7/2010 | Schraga | A61B 5/15146 600/583 |
| 2012/0041383 A1* | 2/2012 | Bruehwiler | A61M 5/008 604/192 |

* cited by examiner

*Primary Examiner* — Kami A Bosworth
*Assistant Examiner* — Hamza Darb

(57) ABSTRACT

A syringe for retracting and storing of the needles for transferring the fluids is provided. The syringe includes a hollow rotatable and retractable syringe plunger body, a hollow syringe barrel slidably disposed inside the hollow rotatable and retractable syringe plunger body a plunger slidably disposed in the hollow syringe barrel, a syringe adapter attached to the front end of the hollow syringe barrel, a syringe plunger adapter attached to the syringe adapter, a hollow retractable barrel body attached to the hollow rotatable and retractable syringe plunger body. The syringe further includes plurality of springs, a first needle and a second needle for injecting and ejecting fluid, on using the first needle, the first needle is retracted and then the second needle stored in the syringe barrel is pushed out the hollow retractable barrel.

7 Claims, 7 Drawing Sheets

SYRINGE FACILITATING RETRACTION OF MULTIPLE NEEDLES

BACKGROUND OF THE INVENTION

1. Field of the Invention

The present invention generally relates to a syringe and more particularly relates to the syringe, as well as to the combination of a syringe and multiple needles, thereby facilitating a user to retract and store one or more needles, thereby improving speed of use of the syringe/needle combination under urgent and emergency circumstances, as well as improving safety by the storage ability of the system.

2. Description of Related Art

A variety of medical fluid injectors exist in which the needles need to be changed frequently to deliver the medical fluid into the body or an infusion system. Part of a health care worker's (for instance a nurse) main role is to safely, efficiently and effectively administer medications to patients. A frequent problem is the shortage in health care (e.g. nursing) staff which results in the health care personnel (e.g. nurses) multitasking and handling more than safely possible. This leads to unsafe practices which were somewhat decreased since the invention of retractable safety needles. Nonetheless, too many health care workers (e.g. nurses) still get pricked by needles while replacing the needles in the syringe, during the withdrawal of the medication and/or administration to the patient and/or needles not being disposed and/or stored safely.

In addition, too many needles are wasted by withdrawing the medication with a large bore (e.g. 18 g) needle from a medication vial and then discarding the 18 g needle to replace it with a smaller gauge (e.g. 21-25 g) needle in order to attach to the syringe. The smaller needle (e.g. 21, 23, or 25 g) needle will be used for inserting the medication into the patient's muscle (e.g. 21-23 g) and/or subcutaneous tissue using an even smaller (e.g. 25 g) size needle. The process for changing the needles is time consuming, which in a health care worker's (for instance a nurse's) emergency situation is unacceptable. It still promotes unsafe practices by having to switch needles which often may come off the syringe (and remain under the patient or under the linen) and/or the practitioner can get pricked during the needle change, and most importantly it is costly.

Current medical fluid delivery devices work on the principle of manually changing or removing the needles used in injectors and furthermore results in unsafe practice. Such devices require considerable time to remove the needle adapters, and further in order to attach to syringe to the IV push port. Therefore, there is a need for a syringe that facilitate a user to retract and store one or more needles, and further the syringe should have required needles stored in the barrel of the syringe.

SUMMARY OF THE INVENTION

In accordance with the teachings of the present invention, a syringe facilitating a user to retract and store a plurality of needles is provided. This also includes the ability to expeditiously and safely switch the required needle size on the syringe.

An object of the present invention is to provide a syringe including a hollow rotatable and retractable syringe plunger body, a hollow syringe barrel slidably disposed inside the hollow rotatable and retractable syringe plunger body, a plunger slidably disposed in the hollow syringe barrel, a syringe adapter attached to the front end of the hollow syringe barrel, a syringe plunger adapter attached to the syringe adapter, a hollow retractable barrel body attached to the hollow rotatable and retractable syringe plunger body.

The syringe further includes plurality of springs disposed in the hollow retractable barrel body, a first needle and a second needle for injecting and ejecting fluid, each needle having a first needle adapter and a second needle adapter, the first needle adapter is attached to the syringe plunger adapter, each needle is disposed in each spring, wherein the hollow rotatable and retractable syringe plunger body forces the syringe plunger adapter to push first needle out and retract from at least one of the plurality of needle openings on application of force by the user.

Furthermore wherein the first needle disengages from the syringe plunger adapter on retracting the hollow rotatable and retractable syringe plunger body and pushing the hollow retractable barrel simultaneously for facilitating and syringe plunger body to align with the second needle on rotation and pushing of the syringe plunger body and further facilitating the second needle to push out from the at least one of the plurality of needle openings.

Another object of the present invention is to provide a syringe plunger seal attached to the plunger for maintaining the consistent movement of the fluid within the hollow syringe barrel. Furthermore, the syringe includes a syringe body lock for locking the syringe with the hollow rotatable and retractable syringe plunger body.

Another object of the present invention is to provide plurality of needle lock for locking each of the needles with each of said springs. The syringe includes one or more syringe plunger lock for locking the hollow rotatable and retractable syringe plunger body and the hollow retractable barrel body.

Another object of the present invention is to provide a syringe plunger body comprising one or more indentations for allowing viewing of movement of fluids inside the hollow syringe barrel. Furthermore, the syringe includes an IV push port attached to at least one of said plurality of needle openings for allowing injection and ejection of fluid when the syringe plunger adapter is rotated and pushed.

Another object of the present invention is to provide a third needle for injecting and ejecting fluid having a needle adapter attached to the syringe plunger adapter on rotation from the syringe plunger body.

Features and advantages of the present invention, as well as the structure and operation of various embodiments of the present invention are described in detail below with reference to the accompanying drawings.

DETAILED DESCRIPTION OF DRAWINGS

Figure 1:
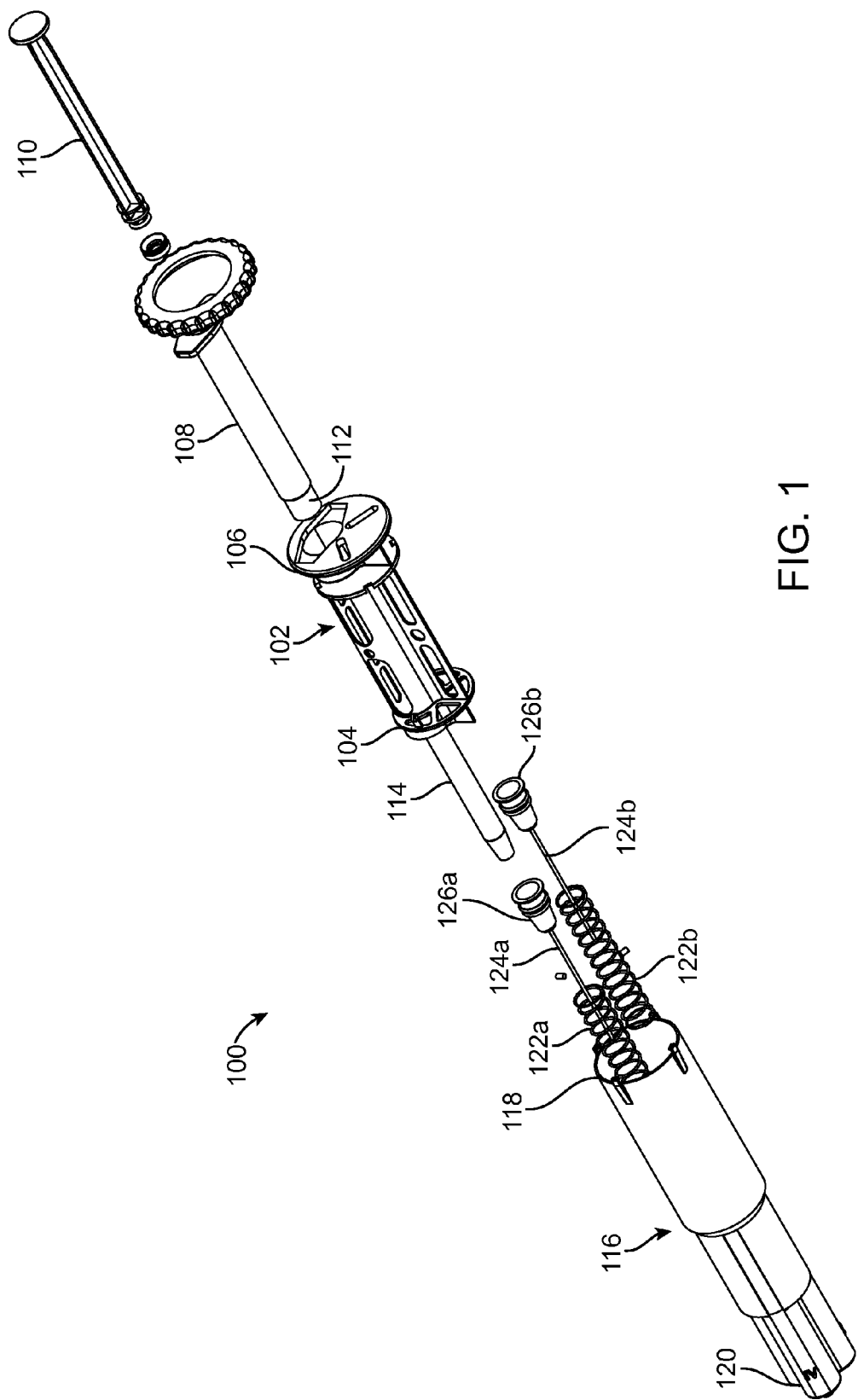
FIG. 1 illustrates an exploded view of the syringe in accordance with a preferred embodiment of the present invention.

While this technology is illustrated and described in a preferred embodiment, a syringe may be produced in many different configurations, forms, and materials. There is depicted in the drawings and will herein be described in detail, as a preferred embodiment of the invention, with the understanding that the present disclosure is to be considered as an exemplification of the principles of the invention, the associated functional specifications for its construction and is not intended to limit the invention to the embodiment illustrated. Those skilled in the art, will envision many other possible variations within the scope of the technology described herein.

FIG. 1 illustrates an exploded view of a syringe 100 in accordance with a preferred embodiment of the present invention. The syringe 100 includes a hollow rotatable and retractable syringe plunger body 102 having a front end 104 and a back end 106, a hollow syringe barrel 108 slidably disposed inside the back end 106 of the hollow rotatable and retractable syringe plunger body 102 for storing fluids.

The syringe 100 further includes a plunger 110 slidably disposed inside the hollow portion of the syringe barrel 108 from the back end 106 of the hollow rotatable and retractable syringe plunger body 102. The arrangement of the plunger 110, the syringe barrel 108 and the hollow rotatable and retractable syringe plunger body 102 is shown and explained in detailed in conjunction with FIG. 3 of the present invention. The plunger 110 controls the movement of the fluid in the hollow syringe barrel 108.

The syringe 100 further includes a syringe adapter 112 is attached to the distal end of the hollow syringe barrel 108. The syringe 100 further includes a syringe plunger adapter 114 attached to the syringe adapter 112 at the front end 104 of the hollow rotatable and retractable syringe plunger body 102.

The syringe 100 further includes a hollow retractable barrel body 116 attached to the back end 106 of the hollow rotatable and retractable syringe plunger body 102. The attachment of the hollow retractable barrel body 116 with the hollow rotatable and retractable syringe plunger body 102 is shown and explained in detail in conjunction with FIG. 5 of the present invention. The hollow retractable barrel body 116 having an open end 118 and a close end 120. The close end 120 includes plurality of needle openings (not shown in FIG. 1). The needle openings are shown and explained in detailed in conjunction with FIG. 4 and FIG. 5 of the present invention.

The syringe 100 includes plurality of springs 122 such as 122a and 122b are disposed in the hollow retractable barrel body 116 from the open end 120. In a preferred embodiment of the present invention, the springs 122 assists the syringe plunger adapter 114 to move back automatically. The syringe 100 further includes plurality of needles 124 such as 124a and 124b for injecting and ejecting fluid from the hollow syringe barrel 108 are disposed in each of the plurality of springs 122. The first needle 124a is having a first needle adapter 126a and the second needle 124b is having a second needle adapter 126b. The first needle adapter 126a is attached to the syringe plunger adapter 114 for transferring the fluid through the plurality of needles 124 from the hollow retractable barrel 108.

In a preferred embodiment of the present invention, when the hollow retractable and rotatable syringe plunger body 102 is attached with the hollow syringe barrel body 116, the first needle 124a moves out through one of the plurality of needle openings (not shown in FIG. 1).

Furthermore, the first needle 124a is retracted and then is disengaged from the syringe plunger adapter 114 on retracting the hollow rotatable and retractable syringe plunger body 102 and extending the hollow retractable barrel body 116 simultaneously for facilitating the syringe plunger adapter 114 to align with the second needle 124b on rotation of the hollow retractable and rotatable syringe plunger body 102.

Furthermore, the hollow rotatable and retractable syringe plunger body 102 is attached with the hollow retractable barrel body 116 to bring the second needle 124b out from at least one of the plurality of needle openings (not shown in FIG. 1). This enables the user to use the plunger 110 to move the fluid either in or out of the hollow syringe barrel 108. The movement from the first needle 124a to the second needle 124b is explained in detailed in conjunction with FIG. 6 of the present invention.

Figure 2:
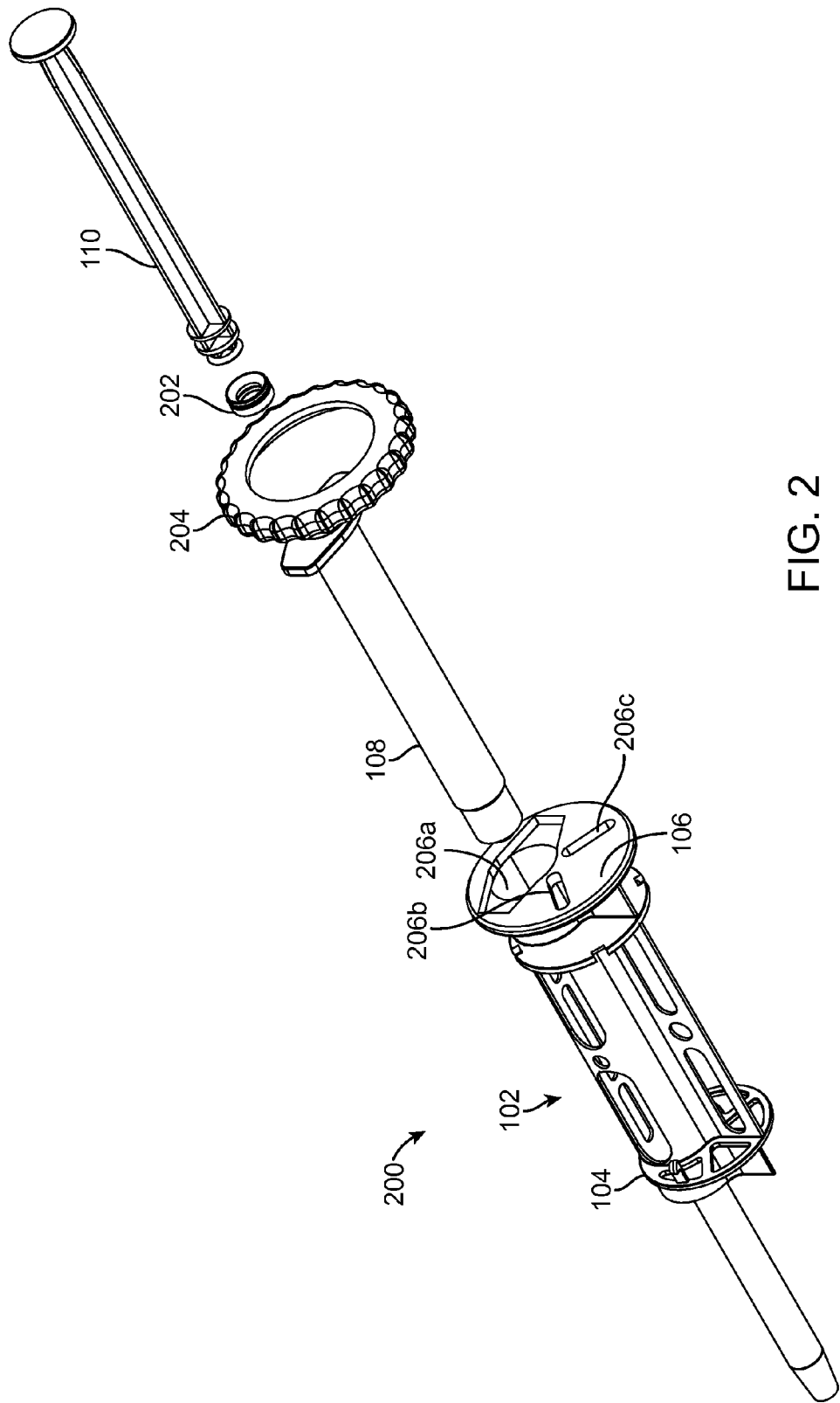
FIG. 2 illustrates another exploded view of the lower body of the syringe in another preferred embodiment of the present invention.

FIG. 2 illustrates another exploded view of the lower body 200 of the syringe in another preferred embodiment of the present invention. The syringe further includes a syringe plunger seal 202 attached to the plunger 110 for maintaining the consistent movement of the fluid within the hollow syringe barrel 108. The plunger seal 202 protects the fluid to come out of the hollow syringe barrel 108. Examples of the material of plunger seal 202 includes but not limited to plastic, rubber etc.

In another embodiment of the present invention, the lower body 200 of the syringe includes a syringe body lock 204 for locking the hollow syringe barrel (not shown in FIG. 2) with the hollow rotatable and retractable syringe plunger body 102. The syringe body lock 204 is configured to be placed on the back end 106 of the hollow rotatable and retractable syringe plunger body 102. The attachment of the hollow retractable barrel body 116 with the hollow rotatable and retractable syringe plunger body 102 is shown and explained in detail in conjunction with FIG. 5 of the present invention In a preferred embodiment of the present invention, the shape of the syringe body lock 204 is circular. However, it will be readily apparent to those skilled in the art that various other shapes of syringe body lock 204 may be configured according to the shape and size of the hollow syringe barrel (not shown in FIG. 1) and the hollow rotatable and retractable syringe plunger body 102.

In a preferred embodiment of the present invention, the back end 106 has plurality of openings 206 such as 206a, 206b and 206c. The opening 206a allows the plunger 110 to enter into the hollow syringe barrel 108 is disposed in the hollow rotatable and retractable syringe plunger body 102.

Figure 3:
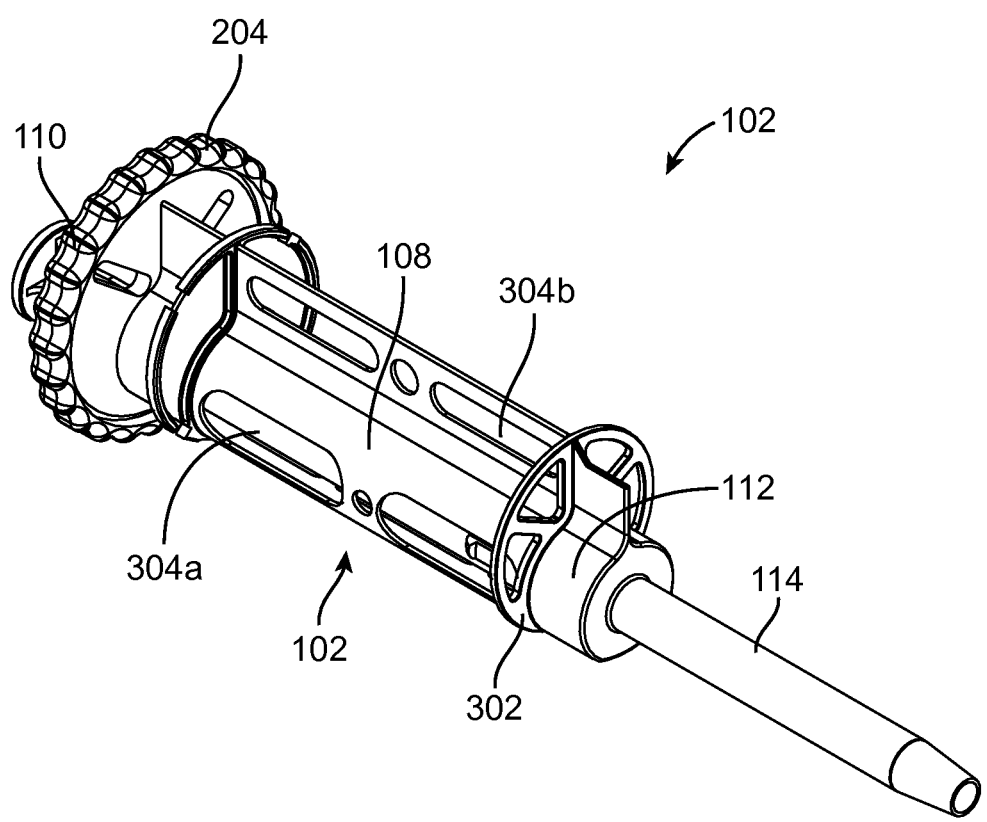
FIG. 3 illustrates a perspective view of a lower body of the syringe in accordance with a preferred embodiment of the present invention.

FIG. 3 illustrates a perspective view of a lower body 200 of the syringe in accordance with a preferred embodiment of the present invention. The plunger 110 is shown to be disposed inside the hollow syringe barrel 108 and the hollow syringe barrel 108 is further disposed inside the hollow rotatable and retractable syringe plunger body 102. The syringe adapter 112 is attached to the distal end 302 of the hollow syringe barrel 108 for allowing the fluid to transfer through needles (not shown in FIG. 3) and the syringe plunger adapter 114 to the hollow syringe barrel 108.

In another preferred embodiment of the present invention, the hollow rotatable and retractable syringe plunger body 102 further includes one or more indentations 304 such as 304a and 304b for allowing viewing of the movement of fluids in the hollow syringe barrel 108.

Figure 4:
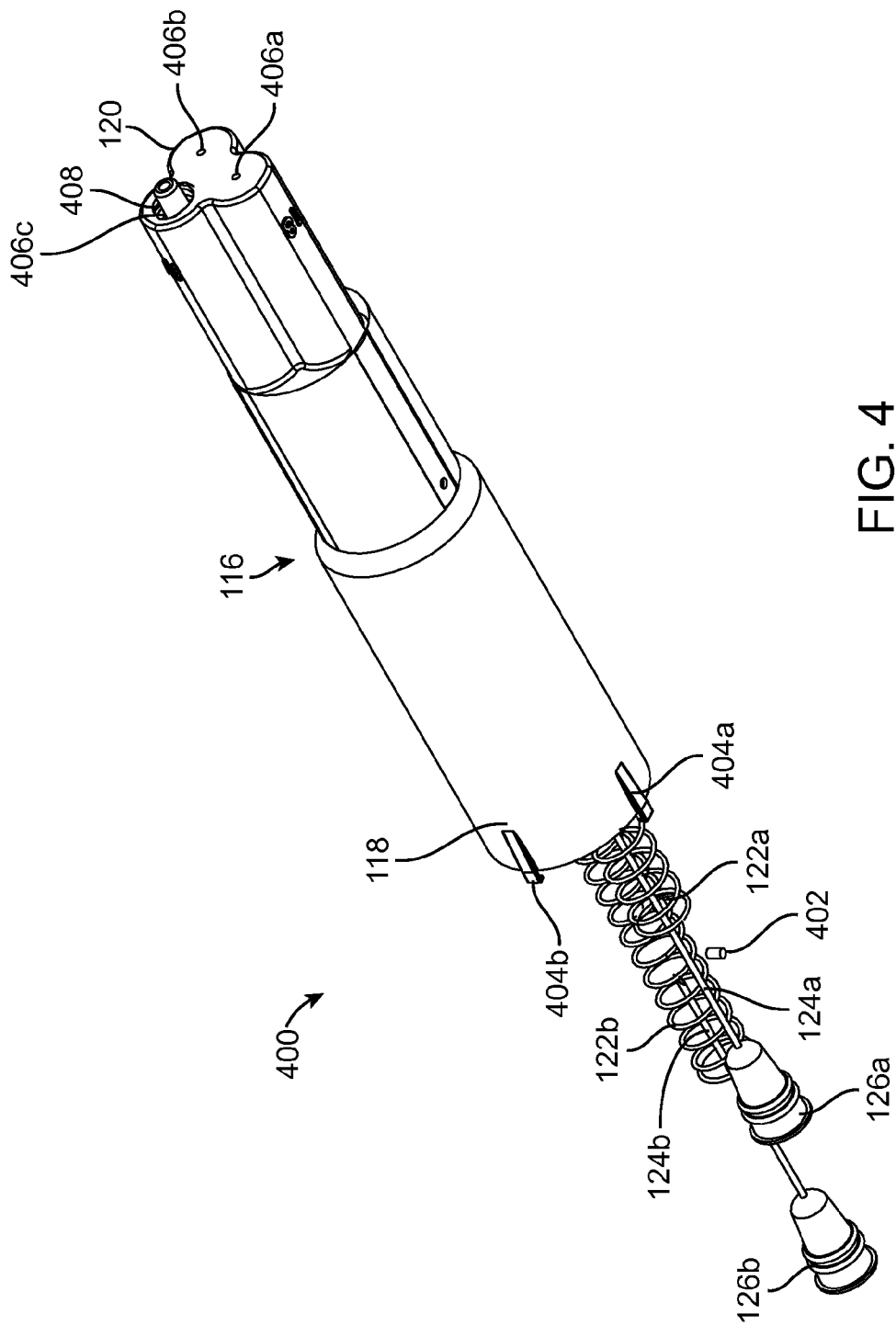
FIG. 4 illustrates another exploded view of the top body of the syringe in a preferred embodiment of the present invention.

FIG. 4 illustrates another exploded view of top body 400 of the syringe in a preferred embodiment of the present invention. In a preferred embodiment of the present invention, the syringe includes one or more needle locks 402 for locking each of the plurality of needles 124. The needle locks 402 maintain the position of needles 124a within the springs 122 for stopping their movement during rotation and retraction of the hollow rotatable and retractable syringe plunger body (not shown in FIG. 4).

In another preferred embodiment of the present invention, the syringe includes one or more syringe plunger locks 404 for locking the hollow rotatable and retractable syringe plunger body (not shown in FIG. 4) and the hollow retractable barrel body 116. The attachment is explained in detailed in conjunction with FIG. 5 of the present invention.

In a preferred embodiment, the syringe plunger locks 404 further sets up the extension level of hollow retractable barrel body 116. The needle adapter 126 does not extend up to the extension of syringe plunger lock 404 for allowing the syringe plunger adapter (not shown in FIG. 4) to detach from the needle adapters 126.

In another embodiment of the present invention, the closed end 120 further comprises plurality of needle openings 406 such as 406a and 406b. The first needle 126a comes out of the needle opening 406a when pushed through the syringe plunger adapter (not shown in FIG. 4) by attaching the hollow retractable barrel body 116 with the hollow rotatable and retractable plunger body 102 and similarly, second needle 126b comes out of the needle opening 406b after disengagement of first needle 124a with the syringe plunger adapter (not shown in FIG. 4). The method of changing from the first needle 126a to the second needle 126b is explained in detail in conjunction with FIG. 6 of the present invention.

In another embodiment of the present invention, the upper body 400 of the syringe includes an IV push port 502 attached to at least one of the plurality of needle openings 406c created on the close end 120 of the hollow retractable barrel body 116 to allow direct intra venous movement of fluids.

The IV Push port 408 comes into use when the syringe plunger adapter (not shown in FIG. 4) disengages with at least one of the plurality of needle adapters 126 by the force applied by a user, then the syringe plunger adapter (not shown in FIG. 4) is rotated and aligned with the axis of the IV Push port 408. The user locks the hollow retractable barrel body 116 with the hollow rotatable and retractable syringe body (not shown in FIG. 4), thus the syringe plunger adapter (not shown in FIG. 4) is made to attach with the IV Push port 408.

Figure 5:
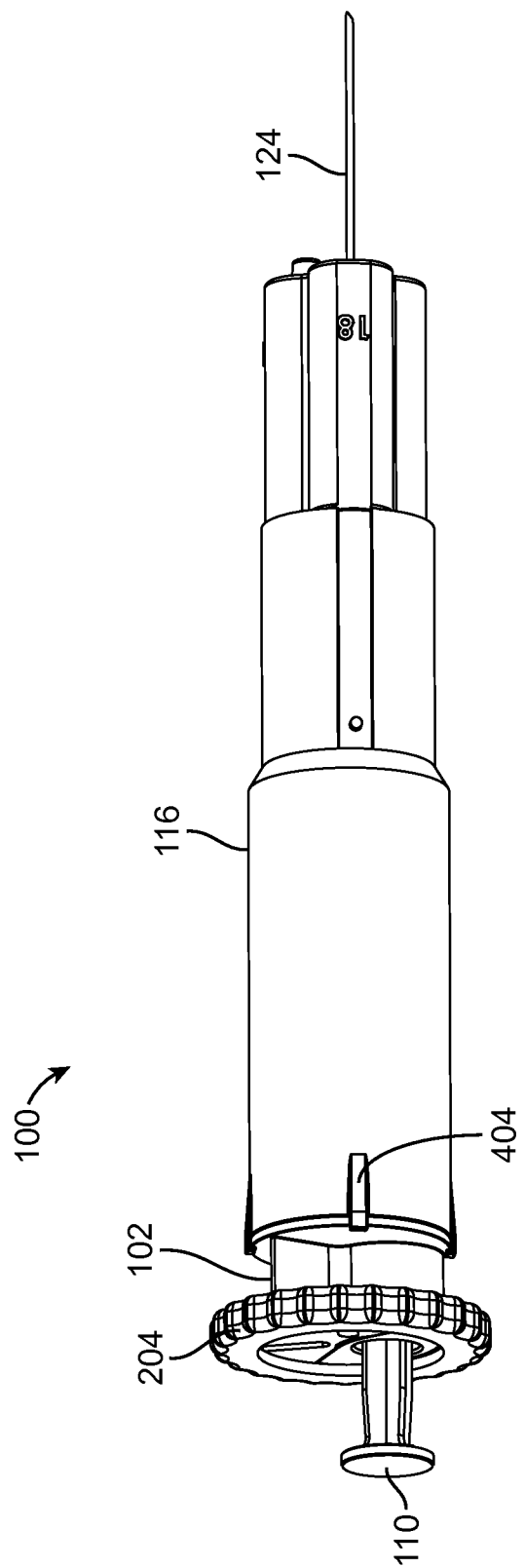
FIG. 5 illustrates a perspective view of the syringe, when the plunger is inside the syringe barrel in accordance with a preferred embodiment of the present invention.

FIG. 5 shows the perspective view of the syringe 100 in accordance with a preferred embodiment of the present invention. The hollow retractable barrel body 116 is attached to the hollow rotatable and retractable syringe plunger body 102 through locking by one or more syringe plunger locks 404 at the syringe body lock 204. The hollow rotatable and retractable syringe plunger body 102 is disposed in the hollow retractable barrel body 116. The syringe plunger lock 404 restricts any relative motion of the hollow retractable barrel body 116 and hollow rotatable and retractable plunger body 102 and pushes the needle 124 out of at least one of plurality of needle openings (not shown in FIG. 5) and thus enables the plunger 110 to move the fluid in and out of the needle 124.

Figure 6:
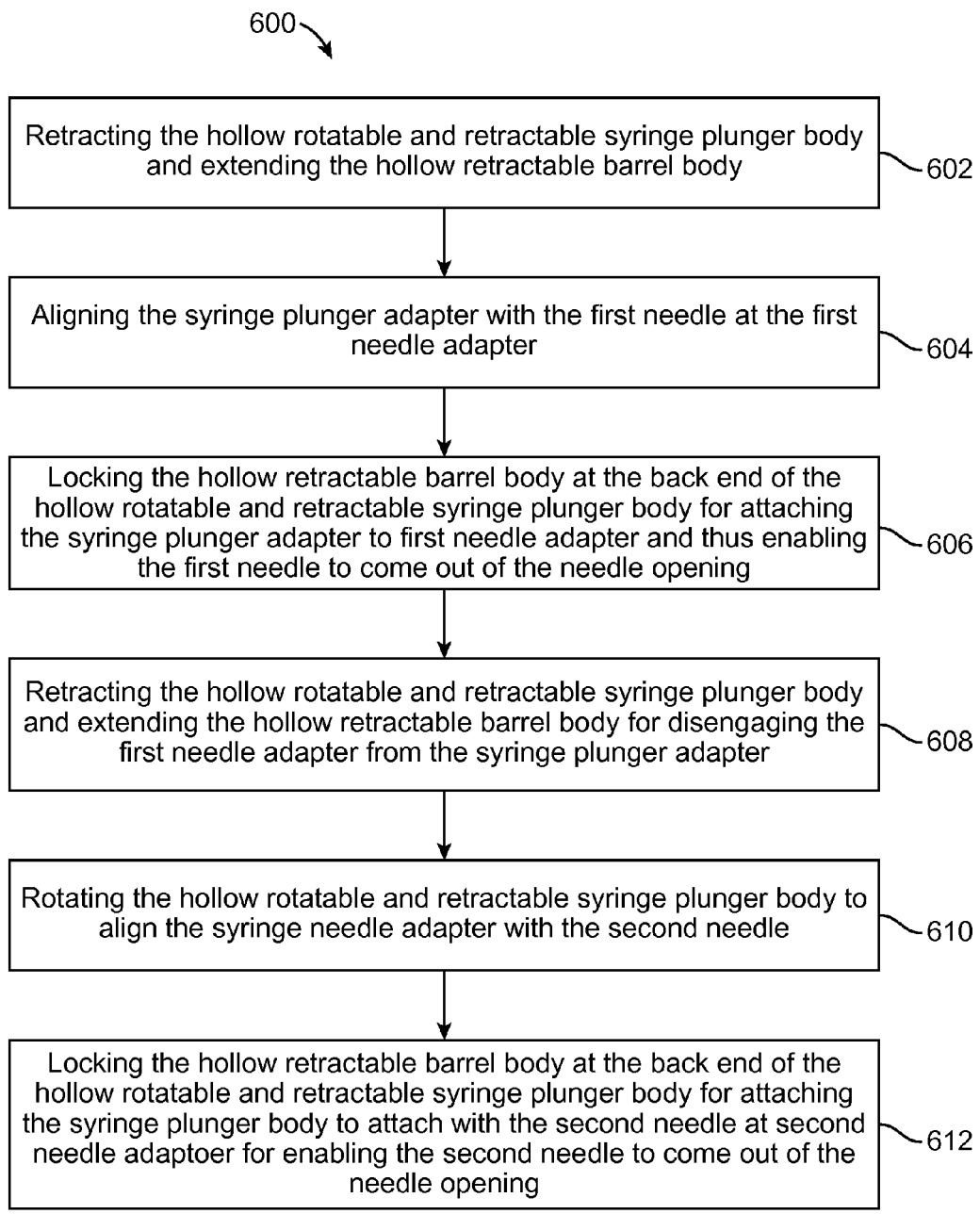
FIG. 6 illustrates a method for changing from a first needle to a second needle in a syringe.

FIG. 6 illustrates a flowchart of a method 600 for changing from a first needle to a second needle in a syringe, in accordance with a preferred embodiment of the present invention. The method 600 initiates with the step 602 of retracting the hollow rotatable and retractable syringe plunger body and extending the hollow retractable barrel body. The retraction of the hollow rotatable and retractable syringe plunger body and extension of the hollow retractable barrel body is explained in detailed in conjunction with FIG. 1 to FIG. 4 of the present invention.

The step 602 is then followed by a step 604 of aligning the syringe plunger adapter with the first needle at the first needle adapter. The alignment of the syringe plunger adapter with the first needle at the first needle adapter is explained in detailed in conjunction with FIG. 1 of the present invention.

The step 604 is then followed by a step 606 of locking the hollow retractable barrel body at the back end of the hollow rotatable and retractable syringe plunger body for attaching the syringe plunger adapter to first needle adapter and thus enabling the first needle to come out of the needle opening. The locking of hollow retractable barrel body with the hollow rotatable and retractable syringe plunger body is explained in detailed in conjunction with FIG. 3 and FIG. 5 of the present invention.

The step 606 is then followed by a step 608 of retracting the hollow rotatable and retractable syringe plunger body and extending the hollow retractable barrel body for disengaging the first needle adapter from the syringe plunger adapter. Further, the retraction enables the first needle to retract back into the hollow retractable barrel body. The retraction of the hollow rotatable and retractable syringe plunger body and extension of the hollow retractable barrel body is explained in detailed in conjunction with FIG. 1, FIG. 2 and FIG. 4 of the present invention.

The step 608 is then followed by a step 610 of rotating the hollow rotatable and retractable syringe plunger body to align the syringe needle adapter with the second needle. The rotation of the hollow rotatable and retractable syringe plunger body to align the syringe needle adapter with the second needle is explained in detail in conjunction with FIG. 1 of the present invention.

The step 610 is then followed by a step 612 of locking the hollow retractable barrel body at the back end of the hollow rotatable and retractable syringe plunger body for attaching the syringe plunger body to attach with the second needle at second needle adapter for enabling the second needle to come out of the needle opening.

In another embodiment of the present invention the method 600 is then followed by the steps of retracting the hollow rotatable and retractable syringe plunger body and extending the hollow retractable barrel body for disengaging the second needle adapter from the syringe plunger adapter; then followed by rotating the hollow rotatable and retractable syringe plunger body to align the syringe needle adapter with the axis of IV push port.

The step is then followed by locking the hollow retractable barrel body at the back end of the hollow rotatable; then followed by retractable syringe plunger body for attaching the syringe plunger body to attach with the IV push port; and then enabling the plunger to control the movement of fluid in the hollow syringe barrel through the IV push port. The steps to attach the syringe plunger adapter with the IV push port are explained in detailed in conjunction with the FIG. 4 of the present invention.

Figure 7:
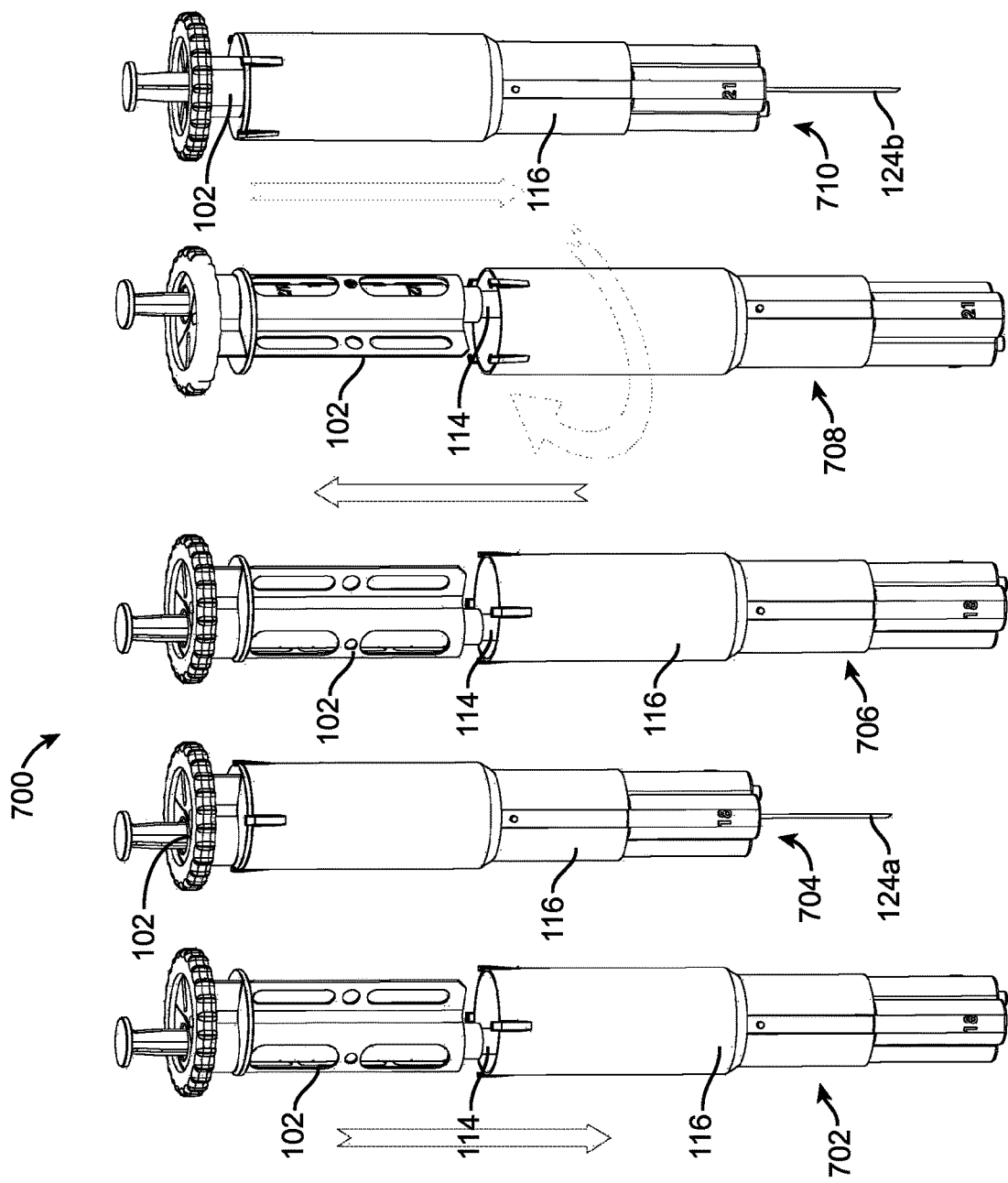
FIG. 7 illustrates a front view, in an exemplary embodiment of the different phases of the syringe for showing exemplary embodiment for changing from the first needle to the second needle of the present invention.

FIG. 7 illustrates a front view in an exemplary embodiment of the different positions of the syringe 700 for showing exemplary embodiment for changing from the first needle to the second needle. Firstly, as shown at position 702, the hollow rotatable and retractable syringe plunger body 102 is retracted and the hollow retractable barrel body 116 is extended to align the syringe plunger adapter 114 with the first needle adapter (not shown in FIG. 7). The position 702 of the syringe 700 illustrates the step 602 and step 604 (reference to FIG. 6), in accordance with an exemplary embodiment of the present invention.

Secondly, as shown at position 704 of the syringe 700, the hollow rotatable and retractable syringe plunger body 102 is locked with the hollow retractable barrel body 116 for enabling the first needle 124*a* to come out of at least one plurality of needle openings (not shown in FIG. 7). The position 702 of the syringe 700 illustrates the step 606 (reference to FIG. 6), in accordance with an exemplary embodiment of the present invention.

Thirdly, as shown at position 706 of the syringe 700, the hollow rotatable and retractable syringe plunger body 102 is retracted and the hollow retractable barrel body 116 is extended to disengage the first needle adapter with the syringe plunger adapter, also enabling the first needle (not shown at position 706) to retract within the hollow retractable barrel body 116. The position 706 of the syringe 700 illustrates the step 608 (reference to FIG. 6), in accordance with an exemplary embodiment of the present invention.

Fourthly, as shown at position 708 of the syringe 700, the hollow rotatable and retractable syringe plunger body 102 is rotated along with the syringe plunger adapter 114 to align it with the second needle (not shown at position 708). The position 708 of the syringe 700 illustrates the step 610 (reference to FIG. 6), in accordance with an exemplary embodiment of the present invention.

Lastly, as shown at position 710 of the syringe 700, the hollow rotatable and retractable syringe plunger body 102 is locked with the hollow retractable barrel body 116 for enabling the second needle 124*b* to come out of at least one plurality of needle openings (not shown in FIG. 7). The position 710 of the syringe 700 illustrates the step 612 (reference to FIG. 6), in accordance with an exemplary embodiment of the present invention.

In a preferred embodiment of the present invention, the first needle is 18 g and the second needle is 21 g. However, it will be readily apparent to those skilled in the art that various other sizes of needles may be stored in the hollow syringe barrel without deviating from the scope of the present invention.

The present invention offers various advantages such as to utilize the syringe retraction with multiple needles has practically with military purposes as well for doctors, nurses, flight surgeons, and combat medical staff. On the battle field and in field hospitals time is the essence and finding different gauge needles may be time consuming when life and death is weighing the balance. Further, needles sticks rise are under intense pressure and medical staff think many times first about their injured soldier and than their own personal safety, thus when people have a chance of having needle sticks, the retractable and rotatable syringe will prevent individuals from sticking themselves.

There has thus been shown and described a syringe which fulfills all the objects and advantages sought therefore. Many changes, modifications, variations and other uses and applications of the subject invention will, however, become apparent to those skilled in the art after considering this specification and the accompanying drawings, which disclose the preferred embodiments thereof. All such changes, modifications, variations and other uses and applications which do not depart from the spirit and scope of the invention are deemed to be covered by the invention, which is to be limited only by the claims which follow.

The invention claimed is:

1. A syringe comprising:
    a hollow rotatable and retractable syringe plunger body comprising a front end and a back end;
    a hollow syringe barrel slidably disposed inside from the back end of said hollow rotatable and retractable syringe plunger body for storing fluids, said hollow syringe barrel having an open front barrel end; and a distal end;
    a plunger slidably disposed inside the hollow portion of said hollow syringe barrel from the back end of said hollow rotatable and retractable syringe plunger body, said plunger controls the movement of the fluid in said hollow syringe barrel;
    a syringe adapter attached to the distal end of said hollow syringe barrel;
    a syringe plunger adapter attached to said syringe adapter at the front end of said hollow syringe plunger body;
    a hollow retractable barrel body attached to the back end of said hollow rotatable and retractable syringe plunger body, said hollow retractable barrel body comprising an open end and a close end, wherein said close end comprising plurality of needle openings;
    a plurality of springs disposed in said hollow retractable barrel body from the open end; and
    a first needle and a second needle for injecting and ejecting fluid from said hollow syringe barrel, said first needle having a first needle adapter and said second needle having a second needle adapter, wherein said first needle adapter attached to said syringe plunger adapter to move the fluid, further each of said plurality of needles disposed in each of said plurality of springs;
    wherein said first needle retracts and disengages from said syringe plunger adapter on retracting said hollow rotatable and retractable syringe plunger body and pushing said hollow retractable barrel body simultaneously for facilitating said syringe plunger adapter to align with said second needle on rotation and pushing of said hollow retractable and rotatable syringe plunger body and further facilitating said second needle to push out and retract from said at least one of said plurality of needle openings.

2. The syringe according to claim 1 further comprising a syringe plunger seal attached to said plunger and enters from the front barrel end of the hollow syringe barrel, further wherein the syringe plunger seal maintains the consistent movement of the fluid within said hollow syringe barrel.

3. The syringe according to claim 1 further comprising syringe body lock for locking said hollow syringe barrel with said hollow rotatable and retractable syringe plunger body.

4. The syringe according to claim 1 further comprising one or more needle locks for locking each of said plurality of needles with each of said plurality of springs.

5. The syringe according to claim 1 further comprising one or more syringe plunger locks for locking said hollow rotatable and retractable syringe plunger body and said hollow retractable barrel body.

6. The syringe according to claim 1 wherein said hollow rotatable and retractable syringe plunger body comprising one or more indentations for allowing viewing of movement of fluids inside said hollow syringe barrel.

7. The syringe according to claim 1 further includes an intravenous push port attached to at least one of said plurality of needle openings, wherein said syringe plunger adapter is rotated and pushed to meet said an intravenous push port for allowing injection and ejection of fluid.

* * * * *